(12) United States Patent
Provost-Tine et al.

(10) Patent No.: US 8,298,210 B2
(45) Date of Patent: Oct. 30, 2012

(54) CATHETER HAVING OVAL ASPIRATION LUMEN AND METHOD OF MAKING

(75) Inventors: Michelle Provost-Tine, North Andover, MA (US); Lee Core, Cambridge, MA (US); Michael Papa, Beverly, MA (US); Michael Riopel, Ipswich, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1495 days.

(21) Appl. No.: 11/259,004

(22) Filed: Oct. 26, 2005

(65) Prior Publication Data
US 2007/0106211 A1    May 10, 2007

(51) Int. Cl.
*A61M 25/00*    (2006.01)
(52) U.S. Cl. ........ 604/527; 604/524; 604/525; 604/526; 604/528
(58) Field of Classification Search ............... 604/93.01, 604/264, 523–525, 527–528, 530, 532–533
See application file for complete search history.

(56) References Cited

U.S. PATENT DOCUMENTS

| | | | | |
|---|---|---|---|---|
| 5,378,230 | A | * | 1/1995 | Mahurkar .................. 604/43 |
| 5,496,275 | A | | 3/1996 | Sirhan et al. |
| 5,743,875 | A | | 4/1998 | Sirhan et al. |
| 5,769,868 | A | | 6/1998 | Yock |
| 5,827,229 | A | | 10/1998 | Auth et al. |
| 5,833,644 | A | | 11/1998 | Zadno-Azizi et al. |
| 6,013,069 | A | | 1/2000 | Sirhan et al. |
| 6,053,904 | A | * | 4/2000 | Scribner et al. ............ 604/527 |
| 6,066,100 | A | | 5/2000 | Willard et al. |
| 6,146,371 | A | | 11/2000 | DeWindt et al. |
| 6,152,909 | A | | 11/2000 | Bagaoisan et al. |
| 6,179,825 | B1 | | 1/2001 | Leschinsky et al. |
| 6,206,849 | B1 | | 3/2001 | Martin et al. |
| 6,270,477 | B1 | | 8/2001 | Bagaoisan et al. |
| 6,447,484 | B1 | | 9/2002 | Briscoe et al. |
| 6,849,068 | B1 | | 2/2005 | Bagaoisan et al. |
| 2002/0026145 | A1 | | 2/2002 | Bagaosian et al. |
| 2002/0177800 | A1 | | 11/2002 | Bagaoisan et al. |
| 2003/0191447 | A1 | | 10/2003 | DeWindt et al. |
| 2004/0116848 | A1 | * | 6/2004 | Gardeski et al. ........... 604/95.01 |
| 2004/0167463 | A1 | | 8/2004 | Zawacki et al. |

FOREIGN PATENT DOCUMENTS

| | | |
|---|---|---|
| EP | 0570102 | 11/1993 |
| EP | 0990449 | 4/2000 |
| WO | WO03045464 | 6/2003 |
| WO | WO03047679 | 6/2003 |

* cited by examiner

*Primary Examiner* — Nicholas D Lucchesi
*Assistant Examiner* — Emily Schmidt

(57) ABSTRACT

Catheters for aspiration of thrombotic, atherosclerotic or other particulate embolic debris from a blood vessel. An elongate flexible aspiration tube has an aspiration lumen defined by a reinforced tube wall. A guidewire tube is secured alongside the aspiration tube extending proximally from a distal end thereof to define either over-the-wire or single operator catheter configurations. The portion of the aspiration tube alongside the guidewire tube has an oval transverse cross section with a minor axis extending transversely through the guidewire tube. The oval cross section of the aspiration tube improves the catheter's efficient use of cross sectional space by making the overall catheter transverse cross section nearly equal in orthogonal dimensions. Methods of making aspiration catheters are also disclosed, including permanently deforming the portion of the aspiration tube into an oval transverse cross section.

12 Claims, 4 Drawing Sheets

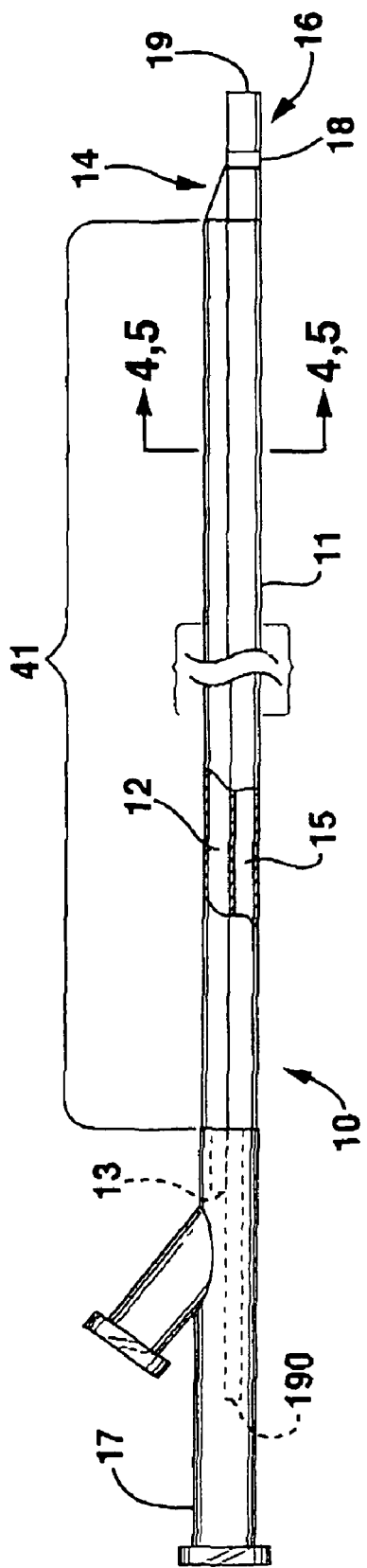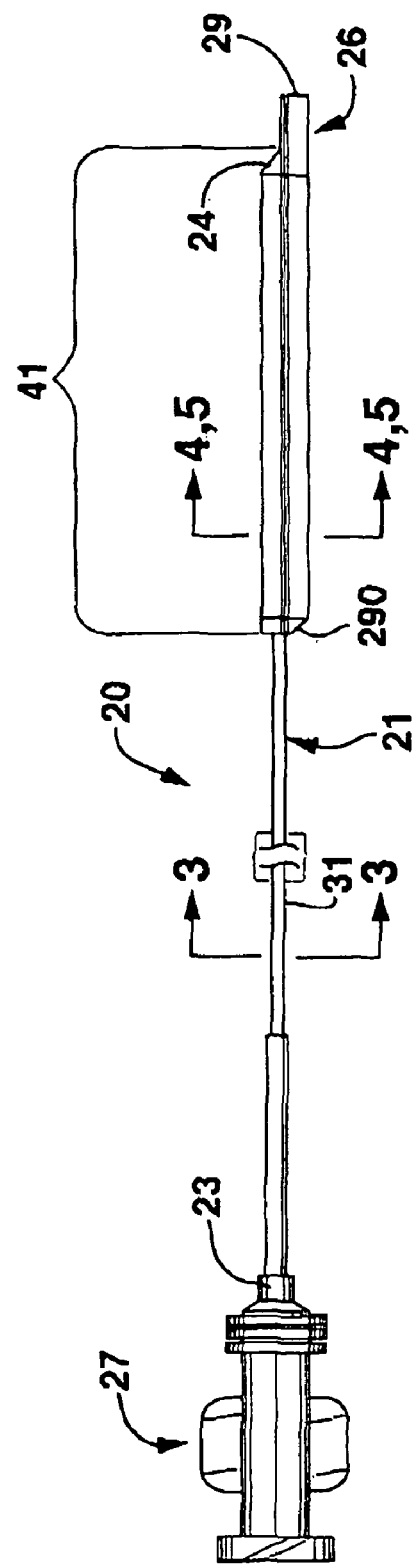

CATHETER HAVING OVAL ASPIRATION LUMEN AND METHOD OF MAKING

FIELD OF THE INVENTION

The present invention relates to aspiration catheters for aspiration of thrombotic, atherosclerotic or other particulate embolic debris from a blood vessel, the apparatus being particularly well suited for aspiration within saphenous vein grafts, arteries in the heart, head and neck, and similar vessels.

BACKGROUND OF THE INVENTION

Human blood vessels often become occluded or completely blocked by plaque, thrombi, other deposits, emboli or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

A serious example of vascular occlusion is coronary heart disease, which is a common disorder in developed countries and is the leading cause of death in the United States. Damage to or malfunction of the heart is caused by narrowing or blockage of the coronary arteries that supply blood to the heart. The coronary arteries are first narrowed and may eventually be completely blocked by plaque (atherosclerosis), and the condition may further be complicated by the formation of thrombi (blood clots) on roughened surfaces of, or in eddy currents caused by the plaques. Myocardial infarction can result from atherosclerosis, especially from an occlusive or near-occlusive thrombus overlying or adjacent to the atherosclerotic plaque, leading to ischemia and/or death of portions of the heart muscle. Thrombi and other particulates also can break away from arterial stenoses, and this debris can migrate downstream to cause distal embolization.

Various types of intervention techniques have been developed to facilitate the reduction or removal of a blockage in a blood vessel, allowing increased blood flow through the vessel. One technique for treating stenosis or occlusion of a blood vessel is balloon angioplasty wherein a balloon catheter is inserted into the narrowed or blocked area, and the balloon is inflated to expand the constricted area. Other types of interventions include atherectomy, deployment of stents, local infusion of specific medication, and bypass surgery. Each of these methods is not without the risk of embolism caused by the dislodgement of the blocking material, which may then move downstream.

Often, more than one interventional catheter is used during a procedure, such as to change the size of the balloon being used or to introduce additional devices into the system to aid with the procedure, including stent delivery catheters and aspiration catheters. In such situations, the catheters are generally inserted into the patient's cardiovascular system with the assistance of a guidewire. For example, a guidewire is introduced into the patient, steered through the tortuous pathways of the cardiovascular system, and positioned across an intended treatment location. Various catheters having a lumen adapted to receive the guidewire may then be introduced into and removed from the patient along the guidewire, thereby decreasing the time needed to complete a procedure.

Many techniques exist for preventing the release of thrombotic or embolic particles into the bloodstream during such a procedure. Common among these techniques is introduction of an occlusive device or a filter downstream of the treatment area to capture these embolic or thrombotic particles. The particles may then be removed from the vessel with the withdrawal of the occlusive or filtering device. In another common technique, the particles may be removed by an aspiration catheter prior to the withdrawal of these devices. Aspiration catheters have also been found useful in removing thrombus prior to crossing underlying atherosclerotic plaque with guidewires and/or treatment catheters. Such preliminary removal of thrombus makes it easier to cross the stenosis and less likely to release thromboembolic particles into the bloodstream during the procedure.

An aspiration catheter may be designed such that a guidewire is contained within the aspiration lumen as the catheter is advanced there over, or the aspiration catheter may include a dedicated guidewire lumen extending along substantially the entire length of the aspiration catheter such that the guidewire is disposed therein as the catheter is advanced through a body lumen. Such dual-lumen catheters having an aspiration lumen and a guidewire lumen may be constructed in a variety of ways including relatively simple profile extrusions, more complex assemblies of different tubular components, and combinations of these two methods.

Dual-lumen profile extrusions can have parallel round lumens surrounded by relatively uniform walls, resulting in a non-circular, generally figure-eight shaped transverse cross section. Alternatively, if a circular outer profile is desired, then dual-lumen profile extrusions can have parallel round lumens with non-uniform wall thicknesses or various other combinations of lumens having unequal sizes and non-round shapes such as D-shapes or crescent-shapes, as will be understood by those of skill in the field of cardiovascular catheters.

One of the important features of aspiration catheters is the ability to rapidly and efficiently aspirate even large embolic particles without the need to first break them into smaller sub-particles. This advantage is achieved, at least in part, by providing the catheter with an aspiration lumen having as large a cross sectional area as possible, given overall size constraints of the catheter design. In embodiments having an aspiration lumen that is crescent shaped or has another non-round shape, a relatively large cross-sectional area is preferably maintained to achieve rapid and efficient aspiration.

Aspiration catheters may also be of the single operator type. A single operator aspiration catheter typically includes a tubular catheter shaft with an aspiration lumen extending the entire length thereof and a substantially shorter guidewire lumen extending along a distal portion of the catheter. As such, the guidewire is located outside of the aspiration catheter except for a short guidewire segment that extends within the guidewire lumen. Advantageously, a clinician is able to control both ends of the guidewire while the aspiration catheter is loaded or exchanged onto the guidewire, which may be already indwelling in the patient. The aspiration catheter is then advanced through the patient's vasculature with only a distal portion of the catheter riding on the guidewire.

Several types of aspiration catheters are disclosed in U.S. Patent Application Publication No. 2002/0177800, which is incorporated by reference herein in its entirety. One of the aspiration catheters in the '800 publication comprises a first elongate flexible tube having a proximal end and a distal end. The first tube incorporates reinforcement such as a metallic braid or coil or a polymer coil to provide strength and flexibility to the device. An aspiration lumen extends the length of the first tube, and an aspiration port at the proximal end of the first tube is in fluid communication with the aspiration lumen, such that partial vacuum for aspiration can be provided through the port and aspiration lumen. A second tube is disposed alongside the first tube and has a lumen adapted to receive a guidewire there through. The second tube can extend substantially the entire length of the first tube, or can extend less than 40 cm in a proximal direction from the distal end of the first tube.

In comparison to dual-lumen extruded catheters, the exemplary aspiration catheter of the '800 publication is assembled from several different components, each of which can be varied or selected to provide desirable features. For example, the disclosed reinforcement may comprise a braid having a varying pitch to advantageously change the flexibility along the length of the aspiration catheter. Alternatively, or in addition, the flexibility of the catheter can be varied by using different polymers to make different portions of the catheter.

As is well known by those skilled in the field of interventional catheterization, guiding catheters are often used when a treatment site is remote from a percutaneous entry point into the patient. Guiding catheters greatly facilitate the navigation or exchange of various devices during a procedure, although their use creates a slightly larger puncture site. It is advantageous to use a guiding catheter with a small outside diameter in a vascular intervention because the time required to close the puncture site is directly related to the diameter of the guiding catheter. Extensive product development has already provided state-of-the-art guiding catheters with very thin walls. Thus, further down-sizing of guiding catheters requires down-sizing of the entire catheter system. That is, guiding catheters having smaller outside diameters also have smaller inside diameters that can only receive interventional devices with concomitantly reduced diameters or transverse outside dimensions.

While the exemplary aspiration catheter of the '800 publication offers numerous performance advantages such as good handling and aspiration efficiency, the catheter is somewhat inefficient in its use of cross-sectional space. To fit the exemplary aspiration catheter of the '800 publication through ever-smaller guiding catheters requires significantly compromising the size of the aspiration lumen in particular, thus reducing the aspiration efficiency of the catheter. There is therefore a need for an improved aspiration catheter that offers an opportunity for reducing the size of the overall interventional catheterization system without diminishing the above stated performance merits of the aspiration catheter.

BRIEF SUMMARY OF THE INVENTION

The present invention provides catheters for aspiration of thrombotic, atherosclerotic or other particulate embolic debris from a blood vessel. An elongate flexible aspiration tube has an aspiration lumen defined by a reinforced tube wall. A guidewire tube is secured alongside the aspiration tube extending proximally from a distal end thereof to define either over-the-wire or rapid exchange catheter configurations. The portion of the aspiration tube alongside the guidewire tube has an oval transverse cross section with a minor axis extending transversely through the guidewire tube. The oval cross section of the aspiration tube improves the catheter's efficient use of cross sectional space by making the overall catheter transverse cross section nearly equal in orthogonal dimensions. Methods for making the aspiration catheter are disclosed, including permanently deforming the portion of the aspiration tube into the oval transverse cross section. The present invention satisfies the need in the prior art by providing an aspiration catheter adapted to be compactly utilized, even in smaller guiding catheters.

The aspiration catheters of the invention are provided with varying flexibility along the length of the shaft, such that they are soft and flexible enough to be navigated through the vasculature of a patient without causing damage, but are stiff enough to sustain the axial push required to position the catheter properly and to sustain the aspiration pressures. The reinforcement layer can be formed as a braid or coil of a polymer or a metal, and a braid or coil density at the distal end can be greater than the braid or coil density at the proximal end to vary the flexibility along the catheter. Radiopaque markers are preferably incorporated into the distal ends of the catheters to facilitate their positioning within the body. The distal tip of the catheter can be tapered, blunt, or angled to create an oblique opening.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a partially-sectioned side view of an aspiration catheter in accordance with the current invention;

FIG. 2 is a side view of another embodiment of an aspiration catheter in accordance with the current invention;

DETAILED DESCRIPTION OF THE INVENTION

Figure 5:
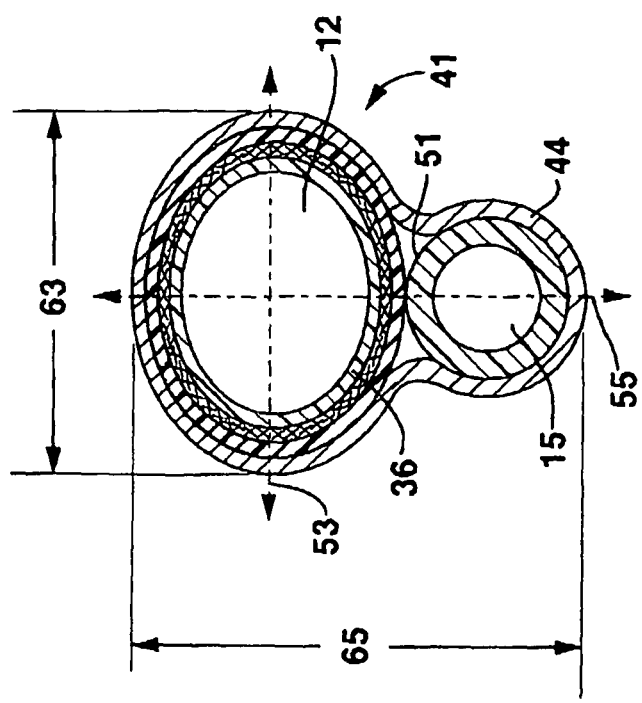
FIG. 5 is a transverse cross sectional view of another embodiment of an aspiration catheter in accordance with the current invention taken along line 5-5 in both FIGS. 1 and 2.

Specific embodiments of the present invention are now described with reference to the figures. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Before and/or after an interventional catheterization procedure has been performed and a stenosis has been removed or reduced using any of the methods and apparatuses described above, the treatment site is aspirated to remove fluid and debris. A source of partial vacuum or "negative pressure" is attached at the proximal end of the aspiration catheter, and fluid and debris are aspirated into the distal end of the catheter, through the aspiration catheter's aspiration lumen, and out of the patient.

An aspiration catheter particularly suited for use in the treatment and removal of occlusions in blood vessels is illustrated in FIG. 1. Aspiration catheter 10 is an over-the-wire catheter having elongate tubular body 11, which comprises two separate lumens, each lumen extending substantially the full length of the catheter. Aspiration lumen 12 fluidly connects first fluid port 13 disposed at or adjacent the proximal end of tubular body 11 with second fluid port 14 disposed at or adjacent the distal end of tubular body 11. Second fluid port 14 is shown forming an optional oblique opening that faces away from guidewire lumen 15. Guidewire lumen 15 is sized and shaped to slidingly accept a medical guidewire there through, and extends from distal opening 19 at catheter distal tip 16 to proximal opening 190 at the proximal end of tubular body 11. Fitting 17 comprising two female luer adaptors is mounted at the proximal end of catheter 10. A first luer adaptor of fitting 17 is in fluid communication with first fluid port 13, and a second luer adaptor of fitting 17 communicates with proximal end 190 of guidewire lumen 15. A source (not shown) of partial vacuum or "negative pressure" may be connected to the first luer adaptor of fitting 17 to aspirate blood and particulates through aspiration lumen 12 of catheter 10. Distal tip 16 can include radiopaque marker 18 to aid in fluoroscopically locating tip 16 during insertion into the patient, and tip 16 is preferably soft to prevent damage to the patient's vasculature.

Figure 3:
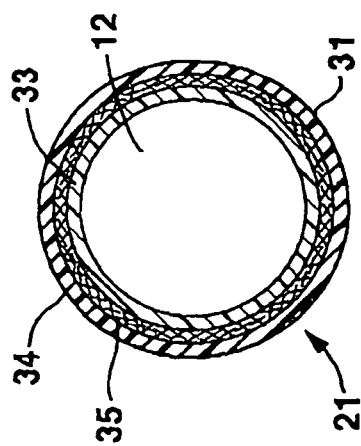
FIG. 3 is a transverse cross sectional view of an aspiration catheter in accordance with the current invention taken along line 3-3 in FIG. 2.

Alternatively, the aspiration catheter in accordance with the invention can be of a rapid-exchange or single operator configuration, as illustrated in FIG. 2, wherein catheter 20 has fitting 27 mounted at the proximal end in fluid communication with aspiration port 23. Like over-the-wire aspiration catheter 10, single operator aspiration catheter 20 comprises elongate tubular body 21 having distal tip 26. Distal tip 26 can also include a radiopaque marker (not shown) to aid in locating tip 26 during insertion into the patient, and tip 26 is preferably soft to prevent damage to the patient's vasculature. Elongate tubular body 21 comprises aspiration tube 31 extending from fitting 27 to a location at or adjacent the distal end of tubular body 21. As shown in transverse cross-section at FIG. 3, aspiration tube 31 comprises a tubular wall that defines single open aspiration lumen 15, which extends the full length of tube 31. The tubular wall of aspiration tube 31 comprises outer jacket 34 adhered about inner liner 33 with reinforcement layer 35 interposed there between.

Single operator aspiration catheter 20 further comprises dual lumen section 41 that is substantially shorter than the full length of catheter 20, extending proximally from second fluid port 24 disposed at or adjacent the distal end of tubular body 21 to open proximal end 290 of guidewire lumen 15. As shown in transverse cross-section at FIG. 4, dual lumen section 41 comprises guidewire tube 51 extending alongside deformed portion 36 of aspiration tube 31 to arrange aspiration lumen 12 and guidewire lumen 15 in a parallel or side-by-side configuration. At least within dual lumen section 41, jacket 34 is absent from aspiration tube 31; jacket 34 having been selectively removed from aspiration tube 31 by a process such as a laser ablation process disclosed in U. S. Pat. No. 6,059,769, which is incorporated by reference herein in its entirety. Within dual lumen section 41, over sleeve 44 surrounds and secures together guidewire tube 51 and deformed portion 36 of aspiration tube 31. Over sleeve 44 can be shrunk and molded into place around guidewire tube 51 and deformed portion 36 of aspiration tube 31 using removable shrink tubing as a tool, similar to the technique described in the '769 patent.

FIG. 5 shows an alternative embodiment of the invention wherein jacket 34 has not been removed from the portion of aspiration tube 31 within dual lumen section 41. In another alternative embodiment (not shown), jacket 34 is removed from a section of aspiration tube 31 proximal to dual lumen section 41. As described in the '769 patent, the removed portion of jacket 34 can be replaced with a filler material having a different flexibility to advantageously vary the stiffness along catheter body 21. An additional section of over sleeve 44 or an alternative polymer resin may be used as the filler material.

Dual lumen section 41, including guidewire lumen 15, can be less than 10 cm in length, but can extend 30 cm or longer in a proximal direction. In the embodiment shown in FIG. 1, dual lumen section 41 extends the full length of over-the-wire aspiration catheter 10. In both catheters 10, 20, aspiration lumen 12 is unobstructed to provide efficient aspiration. During delivery of aspiration catheters 10, 20, the proximal end of a medical guidewire (not shown) is inserted into open distal end 19, 29 of guidewire lumen 15, and guidewire tube 51 is slidingly advanced over the guidewire. A very long medical guidewire (not shown), generally around 300 cm in length, is used to facilitate the insertion of aspiration catheter 10 over the guidewire. Unlike over-the-wire aspiration catheter 10, only a short segment of single operator aspiration catheter 20 rides over the guidewire, which remains in guidewire lumen 15 and does not enter aspiration lumen 12 of the aspiration catheter 20. Thus, single operator aspiration catheter 20 does not require a 300 cm long guidewire and the additional clinician needed to handle it. Instead, aspiration catheter 20 may be used with a medical guidewire having a standard length of about 185 cm. Aspiration catheters 10, 20 may be about 160 cm in length, although this length can be varied as desired.

In both the over-the-wire and single operator type aspiration catheters, the elongate catheter shaft must have sufficient structural integrity, or "stiffness," to permit the catheter to be pushed through the vasculature to remote arterial locations without buckling or undesirable bending of the catheter body. It is also desirable, however, for the catheter body to be fairly flexible near its distal end, so that the catheter may be navigated through tortuous blood vessels. To provide free-sliding movement over a medical guidewire, guidewire tube 51 may be fabricated from flexible low-friction polymers such as polytetrafluoroethylene (PTFE) or a polyolefin. Alternatively, guidewire tube 51 may be made from a polymer selected without regard to its friction properties, and a slippery coating (not shown) can be applied to lumen 15 to reduce friction against a guidewire.

Inner liner 33 and outer jacket 34 may be made from thermoplastic resins that are the same or are at least chemically compatible to permit thermal or solvent bonding between liner 33 and jacket 34 through the interstices of reinforcement layer 35. Examples of suitable thermoplastic resins include amides, polyamides, polyethylene block amides copolymers (PEBA), polyurethanes, and polyolefins such as polyethylenes or polypropylene. Alternatively, inner liner 33 and outer jacket 34 may be incompatible for melt bonding, but can be adhesively bonded together through the interstices of reinforcement layer 35. Over sleeve 44 may also be made of one of the above-mentioned thermoplastic resins that are the same or are at least chemically compatible for thermal or solvent bonding with liner 33 or jacket 34. In an exemplary embodiment, liner 33 is made of 70D durometer PEBA; jacket 34 is made of polyamide; and over sleeve 44 is made of 55D durometer PEBA.

Reinforcement layer 35 can be formed from a braided or coiled filament of stainless steel, work-hardenable nickel-cobalt based superalloy, platinum alloy, refractory metal alloy such as tungsten or tantalum, or a combination thereof. Reinforcement layer 35 is capable of being plastically distorted during manufacture of catheter 10, 20 to retain the shape of deformed portion 36 of aspiration tube 31, as will be described in further detail below. The filaments of reinforcement layer 35 may have a cross-section that is round, oval, flat, or rectangular. The distal region of catheter body 11, 21 is preferably more flexible than the proximal region, and this can be achieved by providing a braid or coil density at the distal end that is greater than the braid or coil density at the proximal end. The braid or coil of reinforcement layer 35 has sufficiently large coil spacing or braid interstices to permit liner 33 and jacket 34 to be secured together there through. In an exemplary embodiment, reinforcement layer 35 comprises a braid of flat stainless steel wire measuring 0.038 mm (0.0015 inch) wide and 0.013 mm (0.0005 inch) thick, the braid having a pick count that varies from about 45 picks per longitudinal inch along the catheter proximal region to about 70 picks per longitudinal inch along the catheter distal region. Pick, or pic, is a term well known to those of skill in the art of catheters and refers to the intersection or crossing of two filaments in a woven tubular braid.

Figure 4:
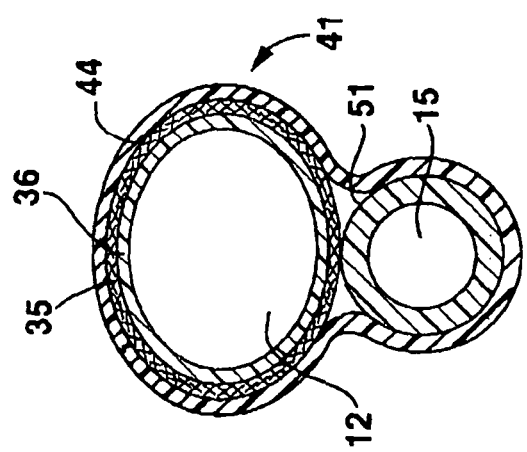
FIG. 4 is a transverse cross sectional view of an aspiration catheter in accordance with the current invention taken along line 4-4 in both FIGS. 1 and 2.

As shown in FIGS. 4 and 5, the transverse cross-section of deformed portion 36 of aspiration tube 31 is generally oval or elliptical in shape, defining major axis 53 extending through the longest dimension of the oval shape, and defining minor axis 55 extending through the shortest dimension of the oval shape. Deformed portion 36 of aspiration tube 31 is oriented with respect to guidewire tube 51 such that minor axis 55 extends through, but not necessarily the center of, adjoining guidewire tube 51. FIG. 5 shows first outside dimension 63 of dual lumen section 41, measured along major axis 53, and second outside dimension 65 of dual lumen section 41, measured along minor axis 55. Outside dimensions 63, 65 can also be measured on other configurations of the invention, including the embodiment shown in FIG. 4. The oval cross section of the aspiration tube improves the catheter's efficient use of cross sectional space by maintaining a sizable aspiration lumen while making the overall catheter transverse cross section nearly equal in orthogonal dimensions, as described below.

Figure 4A:
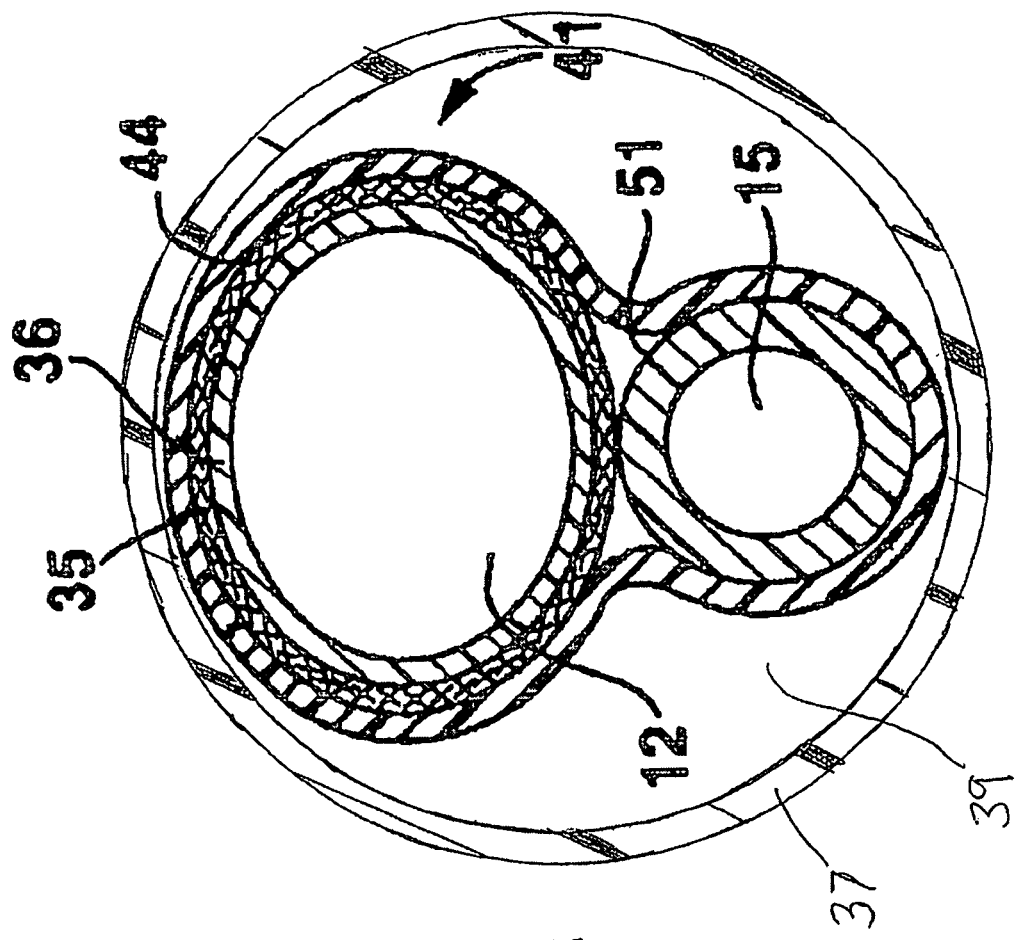
FIG. 4A is transverse cross sectional view, similar to FIG 4, of an aspiration catheter in accordance with the invention contained within the lumen of a guiding catheter.

The following exemplary embodiments of the inventive aspiration catheter are intended for use in human coronary arteries or other small diameter vessels, and are usable through a lumen 39 of a guiding catheter 37 having a diameter no larger than 1.78 mm (0.070 inch) (e.g., FIG 4A). The diameter of guidewire lumen 15 ranges from about 0.381 mm (0.015 inch) to about 0.508 mm (0.020 inch) for receiving a 0.356 mm (0.014 inch) diameter medical guidewire (not shown). Aspiration tube 31 is formed initially with a round lumen diameter of about 1.143 mm (0.045 inch). Deformed portion 36 is subsequently formed in aspiration tube 31 according to the method described below, such that second outside dimension 65 is less than 1.727 mm (0.068 inch). To fit exemplary aspiration catheters 10, 20 through the smallest guiding catheter lumens 39 possible, first outside dimension 63 should remain less than second outside dimension 65 because the cross sectional profile of dual lumen section 41 is not radially symmetrical. The following examples of the invention have been found to have useful proportions between first and second outside dimensions 63, 65.

EXAMPLE 1

|  | First Outside Dimension 63 | Second Outside Dimension 65 | Dim. 63 ÷ Dim. 65 |
|---|---|---|---|
| Pre-Deformation | 1.335 mm (0.053 in) | 1.800 mm (0.071 in) |  |
| Post-Deformation | 1.439 mm (0.057 in) | 1.711 mm (0.067 in) | 84.1% |

EXAMPLE 2

|  | First Outside Dimension 63 | Second Outside Dimension 65 | Dim. 63 ÷ Dim. 65 |
|---|---|---|---|
| Pre-Deformation | 1.545 mm (0.061 in) | 1.749 mm (0.069 in) |  |
| Post-Deformation | 1.633 mm (0.064 in) | 1.666 mm (0.066 in) | 98.0% |

As shown in Examples 1 and 2 above, first outside dimension 63 ranges from about 84% to about 98% of second outside dimension 65. In Examples 1 and 2, first and second outside dimensions 63, 65 are both less than 1.78 mm (0.070 inch) after deformation, such that aspiration catheter 10, 20, will fit slidably through a guiding catheter having an inner diameter of about 1.78 mm (0.070 inch).

Examples 1 and 2 of aspiration catheter 10, 20, also advantageously maximize the size of aspiration lumen 12, given the compatibility constraints stated above: a 0.356 mm (0.014 inch) diameter medical guidewire and a guiding catheter lumen no larger than 1.778 mm (0.070 inch). One way of assessing how efficiently the aspiration catheter utilizes cross-sectional space is to measure the cross-sectional areas of the lumens. In a third example, the transverse cross section of lumen 12 within deformed portion 36 is an oval measuring approximately 1.245 mm (0.049 inch) along major axis 53, and 0.838 mm (0.033 inch) along minor axis 55. The cross-sectional area of lumen 12, assuming an ellipse, is 0.819 square mm (0.00159 square inches). Guidewire lumen 15 having a diameter of 0.394 mm (0.0155 inches) has a cross sectional area of 0.122 square mm (0.000189 square inches). Using the proportions of this exemplary aspiration catheter 10, 20, lumen 12 has a cross sectional area about 6.5 times greater than the cross sectional area of guidewire lumen 15 within deformed portion 36. Thus, in accordance with the invention, aspiration lumen 12 has a cross sectional area at least five times the cross sectional area of guidewire lumen 15 within deformed portion 36.

Figure 7:
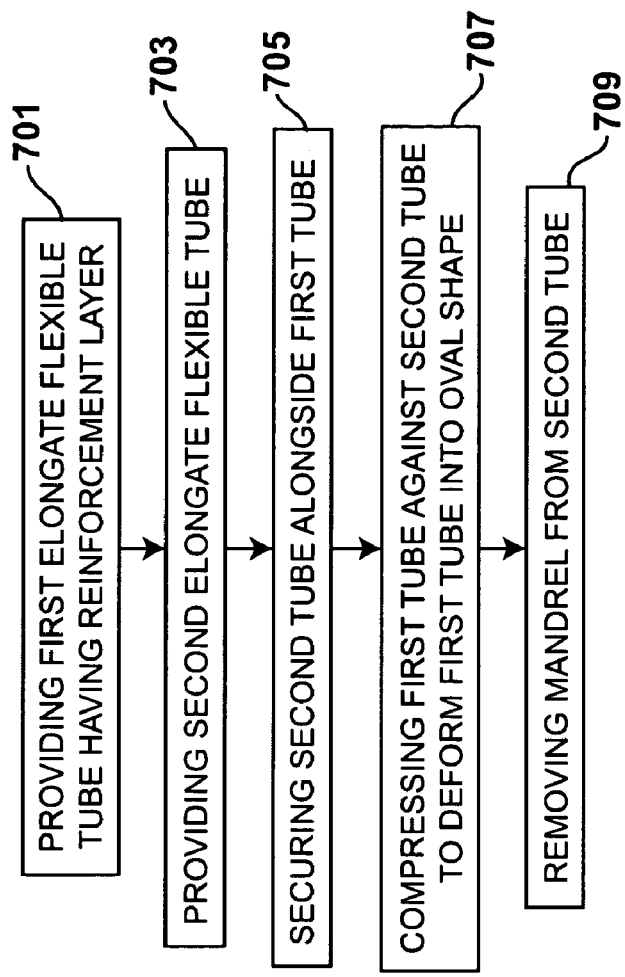
FIG. 7 is flow chart outlining manufacturing steps for an aspiration catheter in accordance with the current invention.

Aspiration catheter 10, 20 is constructed according to the following method, as outlined in FIG. 7. Initial manufacturing step 701 comprises providing a first elongate flexible tube such as aspiration tube 31 having reinforcement layer 35 encapsulated within a wall of the tube. Aspiration tube 31 has only one lumen such as aspiration lumen 12 extending there through. Aspiration tube 31 may be constructed by a reel-to-reel process such as extruding inner liner 33, braiding reinforcement layer 35 around liner 33, and extruding jacket 34 over reinforcement layer 35, as disclosed in the '769 patent, discussed above. Other well-known methods may be used to make the laminated structure of aspiration tube 31.

Manufacturing step 703 comprises providing a second elongate flexible tube such as guidewire tube 51 having lumen 15 extending longitudinally there through and being open at proximal end 190, 290 and distal end 19, 29. Guidewire tube 51 may be made from paste-extruded PTFE or from a melt-extruded thermoplastic as mentioned above. If single operator aspiration catheter 20 is being assembled, then the second elongate flexible tube is selected to be substantially shorter than the first elongate flexible tube.

Figure 6:
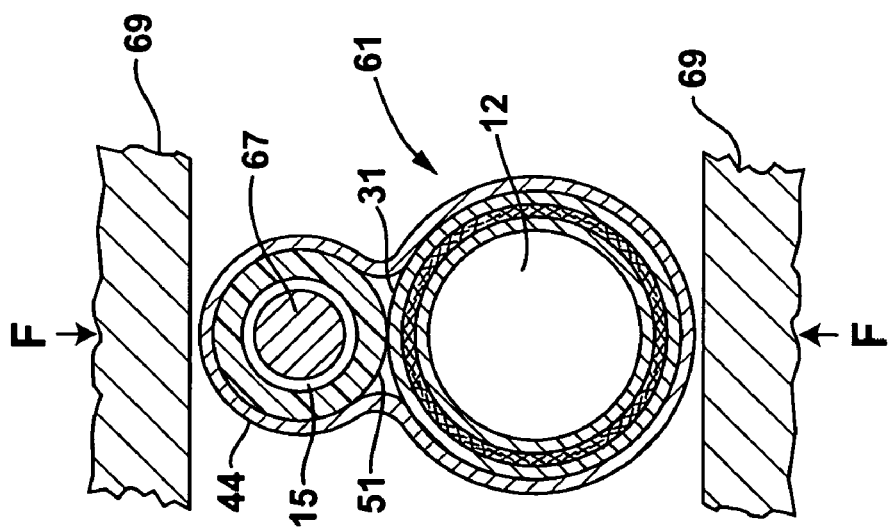
FIG. 6 is a transverse cross sectional view of an aspiration catheter and manufacturing tooling in accordance with the current invention.

Manufacturing step 705 comprises securing the second tube such as guidewire tube 51 alongside the first tube such as aspiration tube 31 using a securement means selected from an adhesive, a solvent bond, and over sleeve 44 surrounding guidewire tube 51 and aspiration tube 31. As discussed above, over sleeve 44 can be shrunk and molded into place around guidewire tube 51 and aspiration tube 31 using removable shrink tubing as a tool, similar to the technique described in the '769 patent. This securement step creates a preliminary, or "un-deformed" dual lumen section 61, as shown in FIG. 6. Optionally, before securing the second elongate flexible tube alongside the first tube, jacket 34 is removed from at least a longitudinal portion of the first tube to be secured to the second tube. Selectively removing jacket 34 reduces outside dimensions 63, 65 of aspiration catheter 10, 20 by eliminating one lamination layer, as shown by comparing FIG. 4 to FIG. 5. If jacket 34 is removed, then guidewire tube 51 is secured directly to reinforcement layer 35 and, through the interstices of layer 35, to liner 33.

FIG. 6 illustrates manufacturing step 707 comprising inserting incompressible mandrel 67 completely through guidewire lumen 15. Aspiration tube 31 is compressed against guidewire tube 51 by application of force F through a fixture that includes a relatively movable pair of jaws, rollers or platens 69. Because guidewire tube 51 is supported by mandrel 67, deformation takes place only in aspiration tube 31 and surrounding over sleeve 34, if used, creating permanently deformed portion 36 of aspiration tube 31. The oval shape of deformed portion 36 is retained substantially by reinforcement layer 35, which has sufficient radial stiffness to overcome any tendency of the plastic layer(s) in aspiration tube 31 to elastically return to the original round cross section shown in FIG. 6. Therefore, it is primarily the compression of reinforcement layer 35 that permanently changes the shape of aspiration tube 31 into deformed portion 36. The stiffness of reinforcement layer 35 makes it optional to use heat to soften any thermoplastic materials of catheter 10, 20 during the compression step.

The compression step may be controlled by limiting the amount of force F, by using physical stops to set a minimum compression dimension between the platens, by inserting an additional incompressible mandrel (not shown) into aspiration lumen 12, or by using a combination of the above controls. An amount of "over-compression" can be performed to compensate for an expected degree of elastic recovery or "spring-back" when compression force F is released. First and second outside dimensions 63, 65 can be measured after the compression step to ensure that desired maximum and relative dimensions have been reached.

Manufacturing step 709 comprises removing mandrel 67 from lumen 15 of guidewire tube 51. Soft catheter tip 16, 26 can be a separate component that is molded onto or otherwise secured at the distal end of catheter 10, 20 at any desired step of the manufacturing process.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An elongate flexible aspiration catheter for removing emboli or other particles from a blood vessel, the catheter comprising:

an aspiration tube having only one aspiration lumen, the lumen defined by an inner surface of a liner and fluidly connecting a first fluid port disposed at the proximal end of the tube and with a second fluid port disposed at the distal end of the tube, a jacket disposed about and adhered to the liner, a reinforcement layer interposed between the jacket and the liner and a deformed portion of the aspiration tube having an oval transverse cross-section defining major and minor axes, that portion of the catheter that includes the deformed portion of the aspiration tube being non-circular in external cross-section;

the aspiration catheter having a guidewire tube extending externally of and alongside only the deformed portion of the aspiration tube wherein the jacket is absent along the deformed portion of the aspiration tube such that the guidewire tube is secured directly to the reinforcement layer and the liner such that the minor axis extends transversely through the guidewire tube, the guidewire tube having a round lumen extending longitudinally therethrough and being open at the proximal and distal ends thereof for slidably receiving a medical guidewire; and a fitting mounted at the aspiration tube proximal end in fluid communication with the first fluid port.

2. The aspiration catheter of claim 1, wherein the deformed portion of the aspiration tube extends continuously from the first fluid port to the second fluid port.

3. The aspiration catheter of claim 1, wherein the deformed portion of the aspiration tube extends a distance of at least about 10 cm proximally from the second fluid port.

4. The aspiration catheter of claim 1 wherein a dual lumen section of the catheter comprising the deformed portion of the aspiration tube has a first outside dimension measured along the major axis of the aspiration lumen cross section and a second outside dimension measured along the minor axis of the aspiration lumen cross section, the first outside dimension ranging from about 84% to about 98% of the second outside dimension.

5. The aspiration catheter of claim 4 wherein the second outside dimension is less than about 1.73 mm (0.068 inches).

6. The aspiration catheter of claim 1 wherein, in a dual lumen section of the aspiration catheter comprising the deformed portion of the aspiration tube, the lumen of the aspiration tube has a cross-sectional area at least five times a cross-sectional area of the lumen of the guidewire tube.

7. The aspiration catheter of claim 6 wherein the lumen of the aspiration tube has a cross-sectional area at least six times the cross-sectional area of the lumen of the guidewire tube.

8. The aspiration catheter of claim 1 wherein the guidewire tube is secured to the aspiration tube by a securement means selected from an adhesive, a solvent bond, and an over sleeve surrounding the guidewire tube and the aspiration tube.

9. The aspiration catheter of claim 1, wherein the jacket comprises two or more materials having different moduli along the catheter.

10. The aspiration catheter of claim 1 wherein the reinforcement layer comprises a tubular braid.

11. The aspiration catheter of claim 10 wherein the tubular braid has two or more regions having different pick counts along the aspiration catheter.

12. The aspiration catheter of claim 1 wherein the second fluid port forms an oblique opening that faces away from the guidewire tube.

* * * * *